US012667268B1

(12) United States Patent
Busiashvili et al.

(10) Patent No.:     US 12,667,268 B1
(45) Date of Patent:          Jun. 30, 2026

(54) DEVICE AND METHOD FOR MONITORING HUMAN HEART RATE AND ALERTING FOR CARDIAC ARRHYTHMIA EVENTS

(71) Applicants: Yuri Busiashvili, Glendale, CA (US);
Ze'ev P Drukker, Miami, FL (US)

(72) Inventors: Yuri Busiashvili, Glendale, CA (US);
Ze'ev P Drukker, Miami, FL (US)

( * ) Notice: Subject to any disclaimer, the term of this patent is extended or adjusted under 35 U.S.C. 154(b) by 61 days.

(21) Appl. No.: 19/253,759

(22) Filed: Jun. 28, 2025

(51) Int. Cl.
*A61B 5/024* (2006.01)
*A61B 5/00* (2006.01)

(52) U.S. Cl.
CPC .......... *A61B 5/02427* (2013.01); *A61B 5/746* (2013.01)

(58) Field of Classification Search
CPC ............................ A61B 5/02427; A61B 5/746
See application file for complete search history.

(56) References Cited

U.S. PATENT DOCUMENTS

| | | | |
|---|---|---|---|
| 11,471,657 B1 | 10/2022 | Busiashvili | |
| 2007/0109491 A1* | 5/2007 | Howell .............. | A61B 5/02433 351/41 |

2018/0014741 A1*  1/2018  Chou .................... A61B 5/6803
2019/0265508 A1*  8/2019  Castañeda ................ G02C 5/12
2021/0379388 A1*  12/2021  Connor .............. A61M 60/531
2023/0157635 A1*  5/2023  Jeyanandarajan ... A61B 5/7282
                                                              600/301

* cited by examiner

*Primary Examiner* — Daryl C Pope
(74) *Attorney, Agent, or Firm* — Ralph D Chabot

(57)                    ABSTRACT

A device and method for monitoring a human heart rate and alerting for cardiac arrhythmia events includes a photoplethysmography sensor attachable to an ear lobe of a human and a housing mountable to an eyeglass frame. The housing contains a processor that analyzes heart rate data to detect when the rate falls below a first threshold indicating bradycardia or exceeds a second threshold indicating tachycardia. Upon detection of an arrhythmia event, the device activates a light-emitting element positioned to be visible within the peripheral field of vision of the wearer. The device may include wireless communication capabilities for transmitting heart rate data to external devices and may be configured in various form factors to enable continuous monitoring. This approach enables timely awareness and response to irregular heart rhythms, enhancing personal health monitoring and safety.

8 Claims, 4 Drawing Sheets

DEVICE AND METHOD FOR MONITORING HUMAN HEART RATE AND ALERTING FOR CARDIAC ARRHYTHMIA EVENTS

FIELD OF THE INVENTION

The present invention relates to the field of cardiac arrhythmia.

BACKGROUND

Cardiac arrhythmia can be classified as abnormal heart rhythms that are either too slow (Bradycardia, under about 40 beats per minute) or too fast (Tachycardia, over about 130 beats per minute). These conditions can pose significant health risks to individuals if left undetected and untreated.

Heart rate can be determined by identifying a mechanical pulse wave peripherally utilizing a photoplethysmography (PPG) sensor. This non-invasive technology allows for continuous monitoring of heart rate by detecting changes in blood volume through the skin.

Various methods have been developed for monitoring human heart rate and detecting cardiac arrhythmias. Traditional approaches often rely on electrocardiogram (ECG) devices that measure electrical signals generated by the heart. These systems typically require multiple electrodes attached to the body and continuous signal acquisition, followed by processing to identify irregular heart rhythms. While effective in clinical settings, such methods can be cumbersome for everyday use and may not provide real-time alerts to the user.

In recent years, there has been growing interest in developing wearable health monitoring devices that are more convenient and less intrusive for users. However, many existing wearable heart rate monitors lack the ability to provide immediate, perceptible alerts to the wearer when dangerous cardiac conditions are detected. This limitation reduces their effectiveness as preventative health tools, particularly for individuals at risk of cardiac events.

Furthermore, existing alert systems often rely on auditory signals or smartphone notifications, which may not be immediately noticeable, especially during sleep or other activities. There remains a need for a monitoring system that can provide timely, perceptible alerts directly within the user's sensory field to prompt immediate action when cardiac arrhythmia events are detected.

SUMMARY OF THE INVENTION

Operably connecting a photoplethysmography (PPG) sensor with a housing mountable to an eyeglass frame so as to provide real-time heart rate monitoring which can timely activate a visual alert provides a novel approach to detection of cardiac arrhythmia events. The device presented comprises a PPG sensor for obtaining heart rate data which is operably connected to a housing containing a light-emitting element positioned to be within the peripheral field of vision of a human wearing the eyeglass frame.

In one embodiment, a PPG sensor is connected by a wired connection to a housing which is used to alert the human experiencing a cardiac arrhythmia event. The housing further comprises a processor which, based on instructions stored in a memory operably connected to the processor, determines whether the heart rate received from the PPG sensor is below a first threshold level or above a second threshold level and if either threshold is crossed, activates a light-emitting element. If the heart rate is below the first threshold level, it is indicative of a Bradycardia event. If the heart rate is above the second threshold level, it is indicative of a Tachycardia event. Preferably, the first threshold level is between 36-44 beats per minute (bpm) and the second threshold level is between 130-150 bpm. Most preferably, the first threshold level is 40 bpm and the second threshold level is 130 bpm. If either threshold level is crossed, the processor will signal the light-emitting element of the housing to activate.

The housing preferably comprises a light-emitting diode (LED) positioned near the anterior portion of the housing and oriented inwardly toward the wearer's head. The orientation of the LED is configured such that light emission is perceptible within the wearer's peripheral field of vision. The LED is operatively coupled to a central processing unit (CPU) and an integrated power supply, both contained within the housing.

In a preferred embodiment, the LED can be either multi-color or a dynamically color-changing LED, enabling discrete color outputs corresponding to either a Bradycardia event or a Tachycardia event. For example, the LED may emit a blue light in response to a Bradycardia event and a red light in response to a Tachycardia event. Activation of the LED in either color mode serves as a real-time visual alert to prompt the wearer to seek immediate medical evaluation.

The PPG sensor is positioned to monitor physiological signals. Preferably, the PPG sensor is positioned on the ear lobe of the user. An alternative location to position the PPG sensor is upon the tragus.

The housing is adapted to be attached or mounted to a temple arm of an eyeglass frame, with the bottom surface of the housing being longitudinally concave to be positioned for frictional engagement with the top and side surface portions of the adjacent temple arm.

In some embodiments, the device includes a multimodal alerting mechanism that extends beyond visual LED alerts. The device may be connectable to, or incorporate haptic actuators configured to generate vibration or tactile alerts perceivable by the wearer. Alternatively, the device may be incorporated into an eyeglass which includes lens dimming capabilities through photochromic or electrochromic materials, providing another form of visual alert through controlled alteration of the eyeglass lenses. The device may further include wireless communication capabilities to enable smartphone-based notifications of heart rate information, expanding the alert mechanisms beyond the wearable device itself.

In further embodiments, the device is connectable to, or incorporates additional sensors beyond the PPG sensor, including inertial measurement units (IMUs), temperature sensors, and other biometric inputs. These additional sensors enable the detection of a broader range of physiological conditions beyond cardiac arrhythmia, such as orthostatic hypotension, atrial fibrillation, sleep apnea, and hypoxia. The combination of multiple sensor inputs enhances the device's ability to detect complex physiological states and provide more comprehensive health monitoring.

In another embodiment, a system is provided to include software and machine learning capabilities to enhance monitoring accuracy and functionality. These features may include the device incorporating a wireless transmitter for communication with mobile applications for displaying real-time and historical heart rate trends, adaptive thresholding that modifies detection parameters based on the wearer's context or baseline physiology, and predictive trend detection through algorithmic learning. The system may implement signal filtering or classification using machine learning algorithms to reduce motion artifacts and identify predictive changes in heart rate prior to threshold breaches.

In alternative embodiments, the system may be configured in various modular and alternative form factors beyond traditional eyeglass frames. These may include invisible glasses (lensless frames), detachable temple sensors, ear cuffs, behind-the-ear wearables, neckbands, headbands, or thin temple-only monitoring devices. The system may also include a detachable or modular temple arm containing the sensors, allowing the sensor unit to be worn separately as a night-time monitoring module, enabling continuous 24-hour monitoring through handoff between daytime and sleep-compatible sensor modules.

The system may further include remote interfaces and data sharing capabilities, such as cloud-based dashboards, caregiver integration, and interoperability via API. These features enable clinicians or caregivers to access cloud-synchronized heart rate data and alert logs generated by the system, facilitating remote monitoring and timely intervention when necessary.

In some aspects, the techniques described herein relate to a device for monitoring a human heart rate and alerting a human of a cardiac arrhythmia event comprising: a photoplethysmography sensor for attachment to an ear lobe of the human, and a housing for mounting on one temple arm of an eyeglass frame to be worn by the human comprising: an input for operable connection to the photoplethysmography sensor, a processor, a memory storing instructions that cause the processor to determine whether a heart rate is below a first threshold to indicate a bradycardia event or above a second threshold to indicate a tachycardia event, and an LED positioned to emit light that will be within a peripheral view of the human, wherein the LED is configured to emit light when the processor determines that the heart rate is either below the first threshold or above the second threshold.

In some aspects, the techniques described herein relate to a method for monitoring a human heart rate and providing an alert to a human in response to a cardiac arrhythmia event comprising steps of: providing a device comprising: a photoplethysmography sensor attachable to an ear lobe of the human, and a housing mountable to an anterior portion of a temple arm of an eyeglass frame comprising: an input for operable connection to the photoplethysmography sensor, and an LED positioned to emit light that will be within a peripheral view of the human wearing the eyeglass frame, monitoring heart rate via the photoplethysmography sensor, determining whether the heart rate is below a first threshold to indicate a bradycardia event or above a second threshold to indicate a tachycardia event, and upon detection of either a bradycardia event or a tachycardia event, activating the LED.

In some aspects, the techniques described herein relate to a device for monitoring a human heart rate and alerting a human of a cardiac arrhythmia event comprising: a photoplethysmography sensor for attachment to an ear lobe of the human, a housing for mounting on one temple arm of an eyeglass frame to be worn by the human comprising: a wired connection to the photoplethysmography sensor, a processor, a power source, a memory storing instructions that cause the processor to determine whether a heart rate is below a first threshold of between 36-44 beats per minute to indicate a bradycardia event or above a second threshold of between 130-150 beats per minute to indicate a tachycardia event, and a multi-color LED positioned near an anterior portion of the housing and oriented inwardly toward a head of the human to emit light within a peripheral field of vision of the human.

DETAILED DESCRIPTION OF THE PREFERRED EMBODIMENT

The figures presented herein are for illustrative purposes and the illustrated parts are not necessarily shown in correct proportion or scale.

Figure 1:
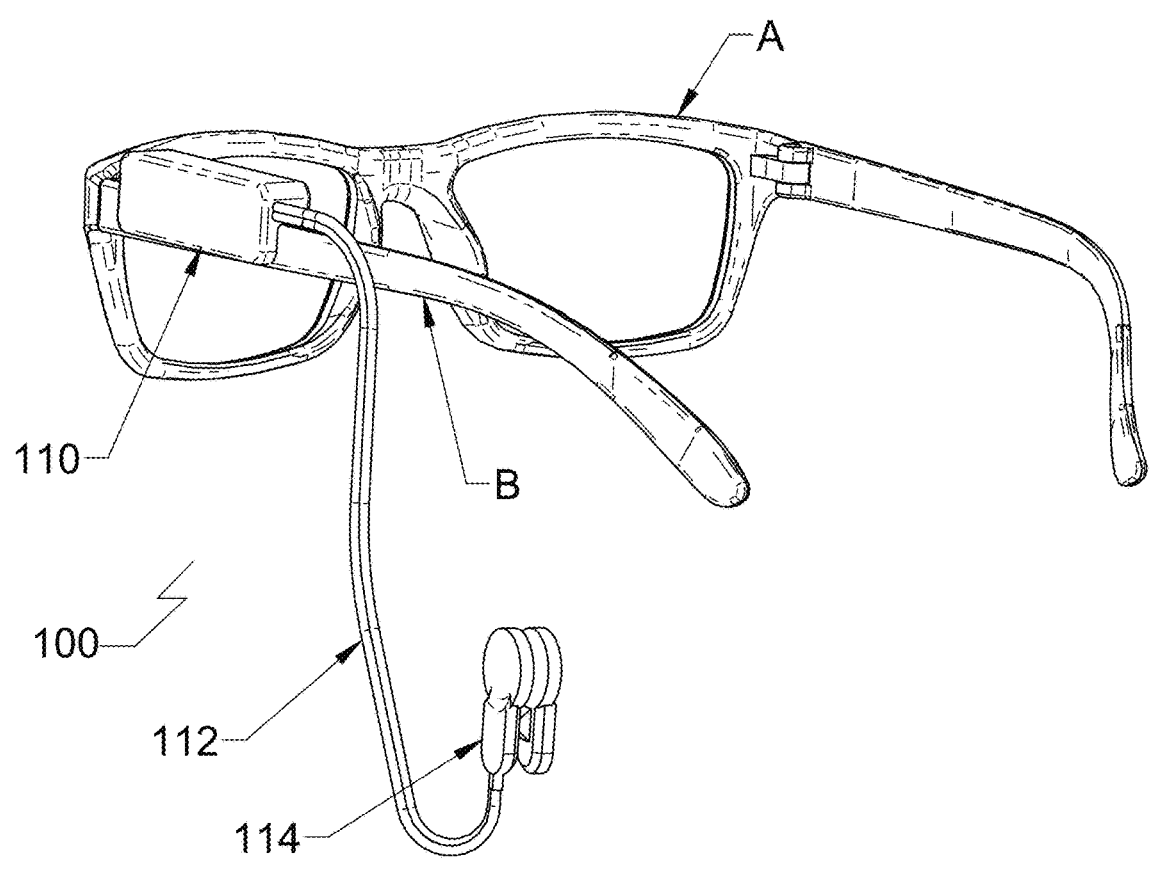
FIG. 1 illustrates the device attached to an eyeglass frame.

As illustrated in FIG. 1, device 100 comprises a housing 110, wired connection 112 and a photoplethysmography (PPG) sensor 114. Housing 110 is adapted to be attached or mounted to a temple arm B of eyeglass frame A. In the embodiment illustrated in FIG. 1, the bottom surface of device 100 is longitudinally concave to be positioned for frictional engagement with the top and side surface portions of the adjacent temple arm B. The concave geometry provides optimal surface contact area to ensure stable mounting during user movement while maintaining a low-profile form factor.

Figure 2:
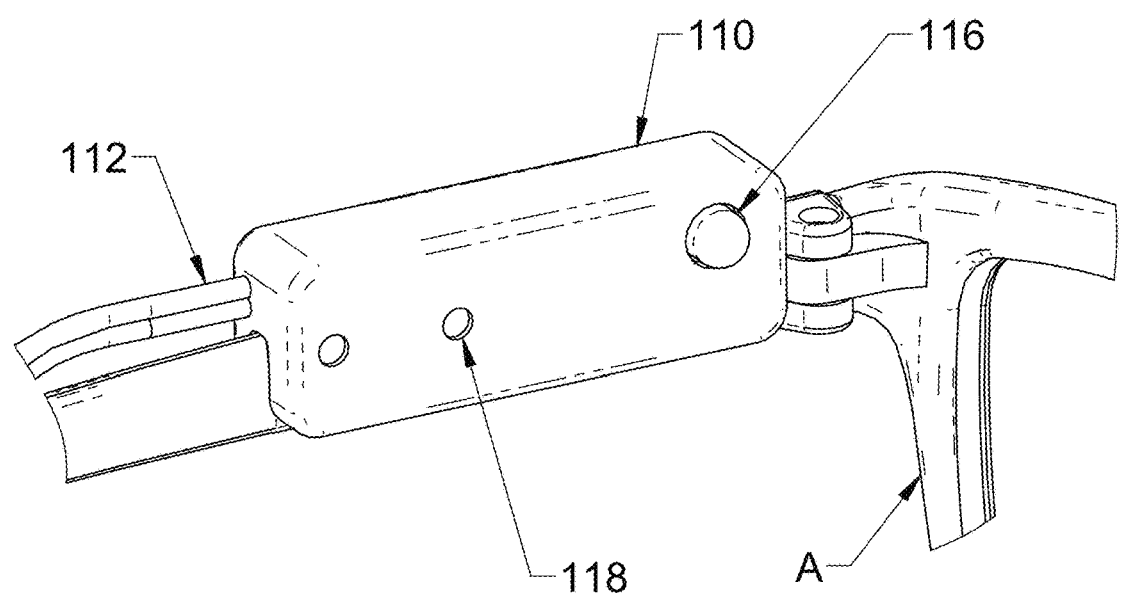
FIG. 2 is a close-up view of the device attached to an eyeglass frame.

As illustrated in FIG. 2, housing 110 comprises a charging port 118 and an LED 116 positioned near the anterior portion of housing 110 to face inward toward the head of a human H. LED 116 is operatively coupled to a central processing unit (CPU) and power source (not shown) within housing 110. The power source preferably comprises a rechargeable lithium-ion battery with sufficient capacity to power continuous monitoring operations for at least 24 hours between charging cycles.

Figure 3:
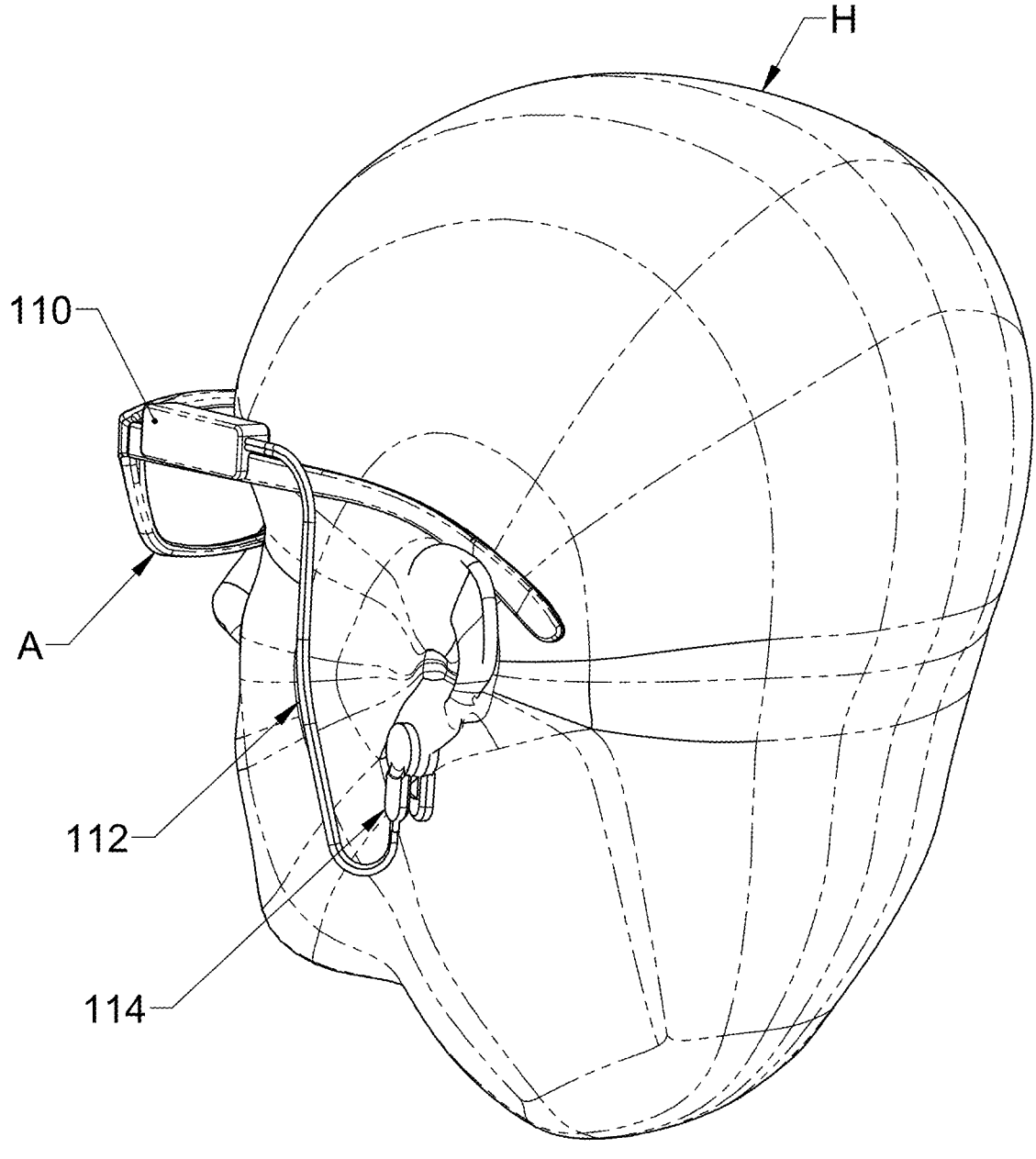
FIG. 3 is a perspective view of the eyeglass frame and device with a PPG sensor attached to an ear lobe.

As illustrated in FIG. 3, PPG sensor 114 is operably connected by wired connection 112 to the CPU and power source within housing 110 and preferably PPG sensor 114 is attachable to an ear lobe of a human H. The PPG sensor 114 utilizes light-emitting and light-detecting components to measure variations in blood volume passing through the microvasculature of the ear lobe tissue, which correlates with cardiac cycles. The sensor samples at a frequency of at least 50 Hz to ensure accurate detection of heart rate variability and arrhythmic events.

Figure 4:
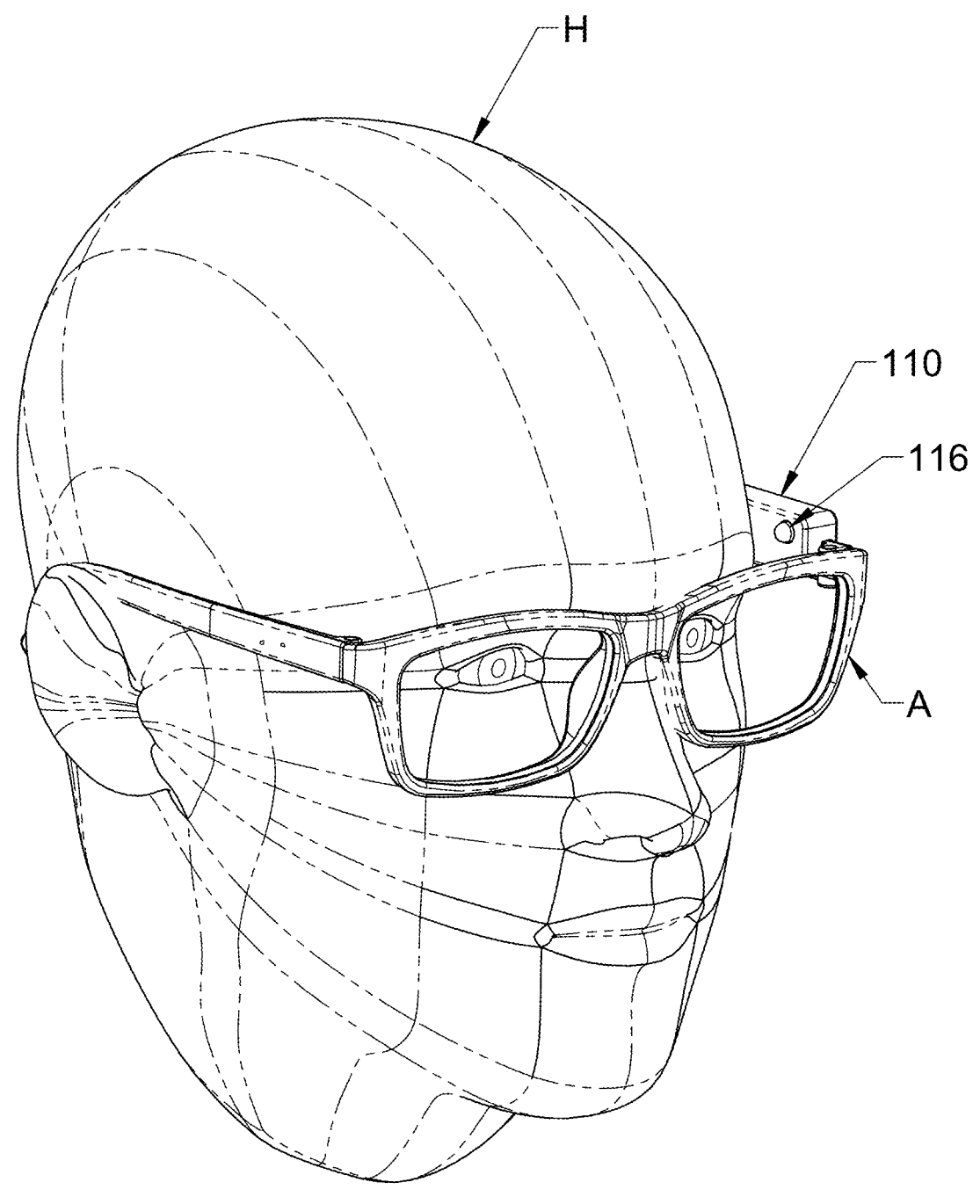
FIG. 4 is a second perspective view of the eyeglass frame and device.

As illustrated in FIG. 4, LED 116 is positioned to be within the peripheral field of vision of the human wearing eyeglass frame A. The LED 116 is specifically oriented at an angle of approximately 30-45 degrees relative to the temple arm to maximize visibility within the wearer's peripheral vision while minimizing direct interference with normal forward vision.

Figure 5:
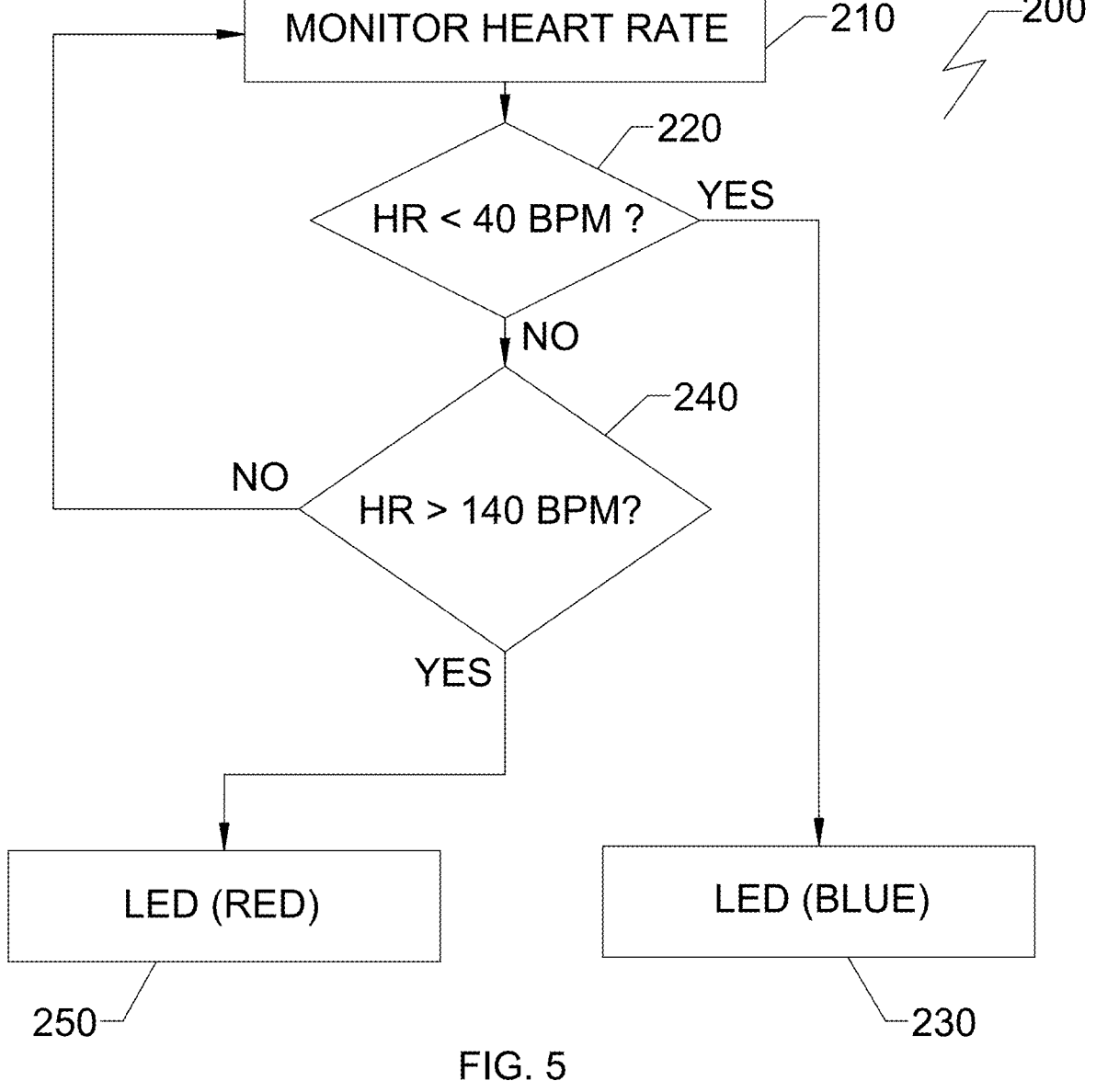
FIG. 5 is a flow chart for a method of use for device operation.

FIG. 5 is a flow chart which describes a method of use 200 for alerting a human of the occurrence of a cardiac arrhythmia event.

At step 210, the CPU continuously monitors the heart rate data received from PPG sensor 114 through wired connection 112. The CPU implements digital signal processing algorithms to filter motion artifacts and ambient light interference from the raw PPG signal, extracting clean inter-beat intervals for heart rate calculation.

At step 220, the CPU determines whether the heart rate data received on a continuous basis is below a first threshold level determinative of a Bradycardia event. The first threshold is a pre-determined value, preferably set between 36-44 beats per minute (bpm). The threshold determination utilizes a rolling average of heart rate measurements over a 10-second window to minimize false positives from transient fluctuations.

If the heart rate data is below the first threshold level, at step 230, the CPU activates LED 116 to emit a blue light. The blue light emission is pulsed at a frequency of 2 Hz to enhance visibility and user attention.

If the heart rate data is above the first threshold level, at step 240, the CPU then determines whether the heart rate data received on a continuous basis is above a second threshold level determinative of a Tachycardia event. The second threshold is a pre-determined value, preferably set between 130-150 bpm. Similar to the bradycardia detection, this determination employs a rolling average calculation to ensure detection reliability.

If the heart rate data is above the second threshold level, at step 250 the CPU activates LED 116 to emit a red light. The red light emission is pulsed at a frequency of 4 Hz, creating a more rapid visual alert pattern compared to the bradycardia alert to intuitively communicate the urgency of a tachycardia event.

When either step 230 (indicative of a Bradycardia event) or step 250 (indicative of a Tachycardia event) occurs, LED 116 is multi-color and emits a respective color within the wearer's peripheral field of vision at a sufficient intensity to ensure perceptibility under daylight conditions, thereby providing an effective visual alert for the human to seek medical attention. The LED illumination persists until manually acknowledged by the user through a capacitive touch sensor integrated into the housing surface or until the detected heart rate returns to normal parameters for a minimum duration of 60 seconds.

In alternative embodiments, the system may incorporate additional sensors including inertial measurement units (IMUs) comprising a 3-axis accelerometer and gyroscope for motion detection and artifact compensation. The IMU data may be fused with PPG signals using Kalman filtering techniques to improve signal quality during physical activity. Temperature sensors may also be integrated to detect changes in peripheral body temperature, which can serve as a complementary indicator for certain cardiovascular conditions.

The system may further implement machine learning algorithms, specifically a lightweight neural network model stored in the device memory, to adaptively adjust detection thresholds based on the individual user's physiological baseline. This personalization improves detection accuracy by accounting for user-specific heart rate variability patterns and reduces false positive alerts by up to 40% compared to static threshold implementations.

For continuous 24-hour monitoring capabilities, the system may include a modular design wherein the sensor unit can be detached from the eyeglass frame and attached to a sleep-compatible wearable form factor. The handoff between monitoring modes is facilitated by near-field communication (NFC) protocols that enable seamless data transfer and monitoring continuity between the daytime and nighttime configurations.

The invention claimed is:

1. A device for monitoring a human heart rate and alerting a human of a cardiac arrhythmia event comprising:
   a photoplethysmography sensor for attachment to an ear lobe of the human; and
   a housing for mounting on one temple arm of an eyeglass frame to be worn by the human comprising:
   an input for operable connection to the photoplethysmography sensor;
   a processor;
   a memory storing instructions that cause the processor to determine whether a heart rate is below a first threshold of between 36-44 beats per minute to indicate a bradycardia event and above a second threshold of between 130-150 beats per minute to indicate a tachycardia event; and
   a multi-color LED positioned near an anterior portion of the housing and oriented inwardly toward a head of the human to emit light within a peripheral field of vision of the human, wherein the LED is configured to emit a first color when the processor determines that the heart rate is either below the first threshold and a second color different from the first color when the processor determines that the heart rate is above the second threshold, wherein the device provides visual alerts only and does not dispense any medication or therapeutic substances.

2. The device of claim 1, wherein the first threshold is 40 beats per minute and the second threshold is 130 beats per minute.

3. The device of claim 1, in which the housing further comprises a charging port.

4. The device of claim 1, in which the housing has a longitudinally concave bottom surface for frictional engagement with a temple arm of the eyeglass frame.

5. The device of claim 1, in which the LED is positioned near an anterior portion of the housing and oriented inwardly toward a human's head.

6. A method for monitoring a human heart rate and providing an alert to a cardiac arrhythmia event comprising steps of:
   providing a device comprising:
   a photoplethysmography sensor attachable to an ear lobe of the human; and
   a housing mountable to an anterior portion of a temple arm of an eyeglass frame comprising:
   an input for operable connection to the photoplethysmography sensor; and
   a multi-color LED positioned to emit light that will be within a peripheral view of the human wearing the eyeglass frame;
   monitoring heart rate via the photoplethysmography sensor;
   determining whether the heart rate is below a first threshold of between 36-44 beats per minute to indicate a bradycardia event and above a second threshold of between 130-150 beats per minute to indicate a tachycardia event;
   upon detection of either a bradycardia event or a tachycardia event, activating the LED upon detection of a bradycardia event, activating the LED to emit a first color; and upon detection of a tachycardia event, activating the LED to emit a second color different from the first color, wherein the method provides visual alerts only without dispensing any medication or therapeutic substances.

7. The method of claim 6, in which the LED emits light at a sufficient intensity to ensure perceptibility under daylight conditions.

8. A device for monitoring a human heart rate and alerting a human of a cardiac arrhythmia event comprising:

a photoplethysmography sensor for attachment to an ear lobe of the human;

a housing for mounting on one temple arm of an eyeglass frame to be worn by the human comprising:

a wired connection to the photoplethysmography sensor;

a processor;

a power source;

a memory storing instructions that cause the processor to determine whether a heart rate is below a first threshold of between 36-44 beats per minute to indicate a bradycardia event and above a second threshold of between 130-150 beats per minute to indicate a tachycardia event; and a multi-color LED positioned near an anterior portion of the housing and oriented inwardly toward a head of the human to emit light within a peripheral field of vision of the human, wherein the LED is configured to emit a first color when the processor determines that the heart rate is below the first threshold and emit a second color different from the first color when the processor determines that the heart rate is above the second threshold, wherein the device provides visual alerts only and does not dispense any medication or therapeutic substances.

\*  \*  \*  \*  \*